United States Patent [19]
Behr et al.

[11] Patent Number: 5,843,894
[45] Date of Patent: Dec. 1, 1998

[54] METHODS FOR REDUCED RENAL UPTAKE OF ANTIBODY FRAGMENTS

[75] Inventors: Thomas M. Behr, Bloomfield; David M. Goldenberg, Mendham, both of N.J.

[73] Assignee: Center for Molecular Medicine and Immunology, Belleville, N.J.

[21] Appl. No.: 407,899

[22] Filed: Mar. 21, 1995

[51] Int. Cl.$^6$ ...................................................... C07K 5/00
[52] U.S. Cl. ........................... 514/12; 530/300; 530/350; 530/324
[58] Field of Search .................... 530/300, 350, 530/324; 514/12

[56] References Cited

U.S. PATENT DOCUMENTS 4,701,521  10/1987  Ryser et al. .............................. 530/322
5,380,513  1/1995  Gray et al. .

FOREIGN PATENT DOCUMENTS 9104755  4/1991  WIPO .

OTHER PUBLICATIONS

Russo et al 1993 Amer. J. Pathology vol. 142 No1 : 261–271.
Batsford et al 1991 Clin. Exp. Immunol. vol. 86: 471–477.
The Webster's II New Riverside Dictionary, Riverside Publishing Company, pp. 72, 1003 and 1269, 1984.
Mogenson et al., *Scand. J. Clin. Lab. Invest.*, 37: 477 (1977).
Hammond et al., *Brit. J. Cancer*, 67: 1437 (1993).
Pimm et al., *Eur. J. Nucl. Med.*, 21: 663 (1994).

*Primary Examiner*—Sheela Huff
*Assistant Examiner*—Julie E. Reeves
*Attorney, Agent, or Firm*—Foley & Lardner

[57] ABSTRACT

Kidney uptake of antibody fragment conjugates in patients is reduced by administration to the patient of one or more compounds selected from the group consisting of D-lysine, poly-D-lysine, or poly-L-lysine, or pharmaceutically acceptable salts or carboxyl derivatives thereof.

12 Claims, 7 Drawing Sheets

METHODS FOR REDUCED RENAL UPTAKE OF ANTIBODY FRAGMENTS

BACKGROUND OF THE INVENTION

This invention relates to a method for reducing renal uptake of monoclonal antibody fragments used for radioimmunodiagnosis (RAID), immunotherapy, and radioimmunotherapy (RAIT). Numerous clinical studies have demonstrated the utility of radiolabeled antibodies for the radioimmunodetection of disease. Antibody fragments, such as Fab', Fab, $F(ab')_2$ and $F(ab)_2$, have faster targeting kinetics than intact immunoglobulin, and are therefore particularly useful for RAID applications. Other advantages of antibody fragments include a much lower occurrence of human immune responses than is found with intact IgG molecules.

A major drawback to the use of radiolabeled antibody fragments for imaging and therapy is the relatively high uptake and retention of radioactivity in the kidney. This phenomenon can impede diagnostic accuracy, especially in the periaortic and epigastric region. and particularly when intracellularly retained isotopes, such as $^{111}$In or $^{99m}$Tc are used. For example, when $^{99m}$Tc-labeled Fab' fragments are used, renal uptakes of up to 25% of the injected dose within 24 h have been reported.

The maximum tolerated dose for a kidney is estimated in external beam radiation is 2000 cGy. Above that threshold the risk of radiation nephritis with subsequent scarring of glomeruli, nephrotic syndrome and renal insufficiency rises considerably. It is likely, therefore that in RAIT using antibody fragments labeled with intracellularly retained radiometals (e.g., $^{90}$Y, $^{168/188}$Re, $^{67}$Cu, $^{177}$Lu) the kidney may become the dose-limiting organ.

Renal uptake of peptides and small proteins is thought to occur via glomerular filtration of molecules smaller than 60 kD, with subsequent tubular reabsorption for lysosomal degradation. When radioisotopes such as iodine are liberated by this degradative process they are released quickly from the cell, but radiometals are retained by binding to ubiquitous intracellular proteins with high affinity for metal ions.

Basic amino acids, such as L-lysine and L-arginine, have been shown to induce functional proteinuria when administered in high dose. Morgenson et al., *Scan. J. Clin. Lab. Invest.* 37:477 (1977). Two previous studies have suggested L-lysine can be effective in decreasing kidney uptake of radiolabeled peptides. Continuous infusion of an amino acid solution containing L-lysine and L-arginine was shown to reduce renal uptake of the $^{111}$In-labeled somatostatin analogue octreotide in humans. Hammond et al. *Brit. J. Cancer* 67:1437 (1993). Repeated intraperitoneal injections of high doses of L-lysine also reduced renal uptake of $^{111}$In-labeled Fab' fragments in BALB/c mice. Pimm et al. *Eur. J. Nucl. Med.* 21:663 (1994).

The requirement for either continuous infusion or repeated injection of amino acids in the methods described by Hammond et al. and by Pimm et al. would cause substantial inconvenience and increased costs in a clinical setting. In addition, the most clinically efficacious dosages of amino acids approach the maximum levels that can be physiologically tolerated before toxicity is observed.

It is apparent, therefore that more convenient methods for reducing renal retention of radiolabeled antibody fragments are greatly to be desired. Methods that are less toxic, and that require fewer and lower dosages are particularly desirable.

SUMMARY OF THE INVENTION

It is therefore an object of the present invention to provide methods that greatly reduce kidney uptake of antibody fragment conjugates.

In accomplishing the foregoing object of the invention, there has been provided, in accordance with one aspect of the invention, a method of reducing kidney uptake of antibody fragment conjugates in a patient during radioimmunodiagnosis or immunotherapy, comprising administering to the patient an effective amount of one or more members compounds selected from the group consisting of D-lysine, poly-D-lysine, and poly-L-lysine, or a pharmaceutically acceptable salt or carboxyl derivative thereof. In a preferred embodiment the poly-D-lysine and the poly-L-lysine each have a molecular weight of 15–30 kDa. In another preferred embodiment the antibody fragment conjugate is a radiolabeled conjugate. In another preferred embodiment the radiolabel is an imaging isotope, and the procedure is radioimmunodiagnosis. In another preferred embodiment the conjugate is a cytotoxic agent and the procedure is immunotherapy.

In accordance with another aspect of the invention there have been provided methods wherein D-lysine, poly-D-lysine, or poly-L-lysine is administered to said patient.

In accordance with yet another aspect of the invention, there has been provided a method wherein a mixture of at least two of compounds selected from D-lysine, poly-D-lysine, and poly-L-lysine is administered to said patient.

There has been provided, in accordance with still another aspect of the invention, a method wherein a compound selected from the group consisting of D-lysine, poly-D-lysine, and poly-L-lysine is parenterally administered to a patient in a physiologically acceptable aqueous solution. In a preferred embodiment the solution is administered by continuous infusion. In another preferred embodiment the solution is administered by means of at least one injection of a bolus of said solution.

In accordance with yet another aspect of the invention, there has been provided a method wherein a compound selected from the group consisting of D-lysine, poly-D-lysine, and poly-L-lysine is orally administered to a patient.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

The present invention provides a means of achieving a significant reduction of the kidney retention of antibody fragment conjugates during RAID or immunotherapy. The reduction is achieved by administration to patients of solutions containing D-lysine alone, or lysine plus poly-lysine, prior to the RAID or RAIT procedure. Additional doses of the solutions may also be administered after delivery of the radiolabeled antibody.

As used herein, a "significant" reduction in renal uptake and retention of radioisotope during a RAID procedure means a reduction at the time of imaging by at least approximately a factor of 2, more preferably a factor of approximately 3 or greater, relative to a procedure in which the solutions of the invention are nor used. Another measure of "significant" reduction in renal uptake and retention of radioisotope is the ability to clearly detect and image a tumor or infectious lesion that is otherwise obscured by high background radiation in the vicinity of the kidney when the solutions of the invention are not used, especially at short imaging times of, e.g. 1–5 hours. In general, the reduction will be most pronounced at short imaging times, affording real advantages to the clinician.

Similarly, a "significant" reduction in renal uptake and retention of radioisotope during immunotherapy means that a dose of antibody fragment conjugate can be used that is at least approximately 2–3 fold times higher than could otherwise be used without risk of kidney damage.

Some radioisotopes that are preferred for RAID applications, such as technetium-99m, have short half-lives (for example, $t_{1/2}$ of Tc-99m is six hours). This means that rapid targeting of an antibody with one of these isotopes is desirable. Antibody fragments such as F(ab')$_2$ and F(ab)$_2$, and especially Fab, Fab', show more rapid targeting kinetics than whole immunoglobulin, and are also associated with a much lower incidence of human anti-murine antibody (HAMA) immune responses. Therefore, they are preferred for RAID applications using isotopes such as Tc-99m.

For immunotherapy applications, whole antibody or bivalent antibody fragments such as F(ab')$_2$ and F(ab)$_2$ are often preferred due to their higher binding constants. Whole antibodies are usually effectively cleared through the liver, and do not pose a significant problem of kidney toxicity. F(ab')$_2$ and F(ab)$_2$ antibody fragments, however, though too large to be effectively filtered through the glomerular basal membrane, nevertheless can still cause significant problems with kidney retention and toxicity during immunotherapy or RAIT.

Previous workers have shown that a continuously infused solution of basic L-amino acids reduced kidney retention of radioactivity in patients being treated with a radiolabeled peptide. See *Hammond* et al., supra. It has also been shown that repeated high doses of L-lysine can reduce the level of retention of radioactivity in the kidneys of mice treated with radiolabeled antibody fragments. See Pimm et al., supra.

In the methods described in the prior work, however, the maximum achievable reduction in kidney retention is limited by the dosage of basic amino acids that can be tolerated without causing toxicity. This toxicity is presumably due to effects of the naturally-occurring L-amino acids on amino acid metabolism. Another drawback to the previous work was that the basic amino acids had to be given repeatedly or continuously to achieve the desired effects.

The present inventors have shown that D-lysine is highly effective in reducing kidney retention of radioactivity in subjects that are treated with radiolabeled antibody fragments. D-Lysine does not occur naturally in humans or animals and is believed to be metabolically inert, thereby reducing the risk of toxic side-effects associated with the use of L-lysine. Mixtures of D- and L-lysine may also be used.

The present inventors have also shown that low doses of poly-lysine, either alone or in combination with monomeric lysine, produce a desirable reduction in kidney retention of radioactivity. It has also been found that poly-lysine or poly-lysine/lysine combinations can be administered at lower dosages and less frequently while still retaining the desired reduction of kidney retention of radioactivity. This leads to a lower overall dosage of amino acids to patients, reducing the risks of toxicity.

The present invention is also useful in immunotherapy applications using antibody fragment conjugates, in which a cytotoxic agent is conjugated to the antibody fragment. Clearance of the fragment through the kidney can lead to kidney damage caused by accumulation of the cytotoxic agent in the kidney. Administration of monomeric or polymeric lysine reduces the accumulation of the cytotoxic agent, and reduces kidney damage.

A. Selection and Labeling of Antibodies

The present invention can be used to reduce the kidney retention of antibody fragments that are radiolabeled by any means currently known or that may be known in the future. The term "antibody fragment" as used herein means a molecule which specifically binds to a complementary antigen and which is derived from a whole immunoglobulin by cleavage, by recombinant methods or by any other process that results in a functional equivalent of a conventional antibody fragment. Examples of suitable antibody fragments include divalent fragments, e.g., F(ab)$_2$, F(ab')$_2$, monovalent fragments, e.g., Fab, Fab', Fv, single chain recombinant forms of the foregoing, and the like. Antibody fragments may be glycosylated, for example containing carbohydrate moieties in the antibody variable regions.

The present invention can be used to reduce the kidney retention of antibody fragments that are radiolabeled with any radioisotope useful for RAID or RAIT. Examples of radioisotopes that are useful for RAID applications are $^{99m}$Tc and $^{111}$In. Radioisotopes that are useful for RAIT include $^{32}$P, $^{90}$Y, $^{186}$Re and $^{188}$Re.

The antibody fragment may be radiolabeled by any method known to the art, or by any method that is discovered in the future. For a discussion of methods for radiolabeling antibody fragments see "Cancer Therapy with Monoclonal Antibodies", D. M. Goldenberg ed. (CRC Press, Boca Raton, 1995). The present invention is useful, therefore, for preventing kidney retention of antibody fragments that are labeled, inter alia, by conjugation of a radiometal-binding chelate, by direct radiometal labeling of hinge region sulfhydryl groups, or by radioiodination via the chloramine-T, iodogen, or Bolton-Hunter methods.

B. Administration of Lysine and Poly-lysine for Therapy and Diagnosis

Generally, the overall dosage of lysine and/or poly-lysine administered to a patient will be that required to reduce the kidney retention of radiolabeled antibody fragment to acceptable levels without causing lysine-induced toxicity. The dosage will vary depending upon such factors as the patient's weight, height, general medical condition, and previous medical history. Any physiologically acceptable salt of lysine or poly-lysine can be used, as can any physiologically acceptable carboxyl derivative of lysine or poly-lysine.

Administration of the monomeric or polymeric lysine or mixture thereof to a patient can be oral, intravenous, intraarterial, intraperitoneal, intramuscular, subcutaneous, or by perfusion through a regional catheter. Administration may be via single or multiple boluses, or by continuous or discontinuous infusion.

The monomeric or polymeric lysine or mixture thereof may be administered in any pharmaceutically acceptable solution. A solution is said to be pharmaceutically acceptable if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 18th Ed. (1990). The concentration of monomeric lysine in the solution is from 3–200 g/l, and that of polymeric lysine is 0.5–100 g/l, although concentrations outside this range may also be used.

An acceptable range for a single dosage of D-lysine administered to a patient is 1–200 g, although a lower or higher dose may be administered. In a preferred embodiment the concentration of lysine in the solution is between approximately 2–35 g/l. In another preferred embodiment, the concentration of lysine in the solution is 15–25 g/l.

Monomeric lysine may need to be administered more than one time to a patient to achieve the desired reduction in kidney uptake. In a preferred embodiment for RAID protocols, monomeric lysine is administered to a patient approximately 30 minutes prior to injection of the labeled antibody fragment, and is then readministered at approximately 1, 2, and 4 hours post-injection. Additional doses of lysine may be given at periodic intervals as deemed necessary to maintain the desired reduction in kidney uptake of radioactivity. In another preferred embodiment suitable for use in both RAID and RAIT protocols, the monomeric lysine is infused at a continuous rate, beginning approximately 30 minutes prior to injection of the labeled antibody. For RAID protocols, administration of lysine can be ended as soon as the imaging process is complete. For RAID protocols, in which much greater amounts of radioactivity are used, administration of lysine is continued until at least 2–3 days after antibody injection.

Equivalent effects on kidney uptake can be achieved with significantly lower doses of poly-lysine than is needed for monomeric lysine. Either D-, D/L- or L-poly-lysine, or any mixture thereof, may be used. The molecular weight range of the poly-lysine may be from 1–60 kDa, although higher molecular weight polymer could also be used. In a preferred embodiment the poly-lysine has a molecular weight range of approximately 1–4 kDa. In another preferred embodiment the poly-lysine has a molecular weight range of approximately 15–30 kDa.

In a preferred embodiment the dosage of poly-lysine administered to a patient in a single bolus is 1–50 mg. Repeated dosage or continuous infusion of poly-lysine is typically not required for RAID applications, but may be needed for prolonged RAIT protocols. The concentration of poly-lysine in the solution is typically 1–50 g/l, though concentrations outside this range may also be used.

The present inventors have also found that use of mixtures of monomeric and polymeric lysine can reduce uptake of radioactivity in the kidney to a similar or greater extent than monomeric lysine alone, but with less frequent administrations. Any combination of D- or L-lysine and D-, D/L, or L-poly-lysine may be used to achieve this effect. The molecular weight range of the poly-lysine used in the mixtures is preferably the same as when poly-lysine is used alone, as described supra. The dosage of monomeric lysine administered to a patient in the mixture is typically from 1–200 g, and that of polymeric lysine is typically from 1–50 mg. In both cases, however, a lower or higher dose may be used. In a preferred embodiment of the invention the dosage of monomeric lysine administered to the patient in a single bolus of the mixture is 2–35 g and that of polymeric lysine is 5–25 mg. The concentration of monomeric lysine in the solution is typically between 3–200 g/l, and that of polymeric lysine is 0.5–100 g/l. In a preferred embodiment the concentration of monomeric lysine in the solution is between 2–35 g/l, and that of polymeric lysine is 10–25 g/l.

C. Determination of Effects on Kidney Uptake of Radioactivity

Initial dosage ranges for achieving the desired reduction in kidney uptake of radioactivity can be determined by using standard animal model systems. Animals are injected with radiolabeled antibody fragments and the level of kidney uptake is compared in animals that are treated with different amounts of lysine or lysine-containing compounds. The results obtained are compared to the results obtained in control animals which receive only the radiolabeled antibody fragments.

A preferred model system is the mouse. For determining the reduction of kidney uptake in non-tumor-bearing subjects the preferred mouse strain is BALB/c mice (Charles River Laboratories, Boston, Mass.). The preferred strain for determining reductions in tumor-bearing subjects is athymic mice (Harlan, Madison, Wis.), carrying an engrafted human tumor, such as that produced by subcutaneous injection of the human colon carcinoma cell line GW39 (Primus et al., Cancer Res. 33:2977 (1973). Mice are injected intravenously into the tail vein with approximately 5–10 µg of radiolabeled antibody fragment protein. Typical doses of radioactivity are 25–40 µCi of $^{99m}$Tc, $^{188}$Re, or $^{111}$In, 4 µCi of $^{88}$Y, and 10 µCi of $^{125}$I. The mice are sacrificed at predetermined time periods after injection of the labeled antibody fragments, for example at 4 h and 24 h for $^{99m}$Tc, and at 4, 24, 72, 96 and 168 h for $^{125}$I, $^{111}$In, $^{88}$Y and $^{188}$Re-labeled antibodies. The mice are sacrificed and dissected and the amount of activity in the kidney is determined by standard methods. An injection standard is used to correct for radioactive decay. Comparison of the results in the control mice with those in the mice that receive the lysine and/or poly-lysine allows determination of the optimal dosage required to achieve the desired effect on kidney uptake of radioactivity. Determination of the dosage of lysine and/or poly-lysine that can be tolerated before toxic effects are observed can be achieved by physiological examination and histological observation of organs by methods. The optimal dosages of lysine and/or poly-lysine that are determined using the mouse model is used to guide the determination of appropriate dosage levels in human subjects using a standard dosage escalation regimen. Methods for determining effective dosages of lysine and/or poly-lysine for reducing kidney uptake are further illustrated in the Examples, below. Kits containing RAID and RAIT reagents can advantageously include monomeric and/or polymeric lysine.

The present invention, thus generally described, will be understood more readily by reference to the following examples, which are provided by way of illustration and are not intended to be limiting of the present invention.

EXAMPLES

General Methods

Preparation of Radiolabeled Antibody Fragments

The murine monoclonal anti-carcinoembryonic antigen (anti-CEA) antibody NP-4 and the second generation antibody anti-CEA MN-14 have been described previously (Sharkey et al., Cancer 71:2082 (1993). The anti-colon-specific antigen-p (CSAp) antibody Mu-9 and the anti-B-cell lymphoma (anti-CD22) antibody LL2 (EPB2) have also been reported. See Blumenthal et al., Cancer Immunol. Immunother. 32:303 (1991) and co-pending U.S. application Ser. No. 08/289576. Antibodies were purified from mouse ascites fluid by standard methods using protein A and ion-exchange chromatography on S- and Q-Sepharose (Pharmacia, Piscataway, N.J.) at 4° C. Purity was ascertained by immunoelectrophoresis, sodium dodecylsulfate polyacrylamide gel electrophoresis (SDS-PAGE) and isoelectric focusing.

All antibody fragments were prepared by standard methods. F(ab')$_2$ fragments of the NP-4, Mu-9 and LL2 antibodies were prepared by pepsin digestion, and F(ab)$_2$ fragments of MN-14 were generated by papain digestion. The fragments were purified by protein A chromatography on Protein A-Sepharose (Pharmacia), using the conditions recommended by the manufacturer. Fab' fragments of NP-4, LL2 and Mu-9 were generated from the corresponding F(ab')$_2$ fragments, and the Fab fragment of MN-14 was generated from the corresponding F(ab)$_2$ fragments by reduction with cysteine using standard methods.

Fab' fragments NP-4 and LL2 were prepared for $^{99m}$Tc-labeling by following the method described in U.S. Pat. No. 5,061,641. For $^{188}$Re-labeling, Fab' fragments of Mu-9 and LL2 containing free sulfhydryl groups were prepared by reduction with 2–20 μM 2-mercaptoethanol for 10 min at 4° C. The reaction products were purified by gel filtration chromatography, mixed with stannous tartrate in 50 mM PBS, pH 5.3, lyophilized and stored under an inert atmosphere.

For $^{111}$In and $^{88}$Y-labeling, isothiocyanate benzyl-DTPA (SCN-Bz-DTPA) conjugates of the F(ab)$_2$ and Fab fragments of MN-14, and the F(ab')$_2$ fragment of LL2 were prepared by adding SCN-Bz-DTPA to the antibody (5.0 mg/ml), previously dialyzed against 100 mM Hepes buffer, pH 8.6, containing 150 mM NaCl, at a 8:1 molar excess of DTPA to MAb. After overnight incubation at room temperature, the antibody conjugates were purified from unreacted SCN-Bz-DTPA by gel filtration chromatography on a 1×50 cm column of Sephadex G-50 (Pharmacia).

Technetium-99m was obtained from a $^{99}$Mo/$^{99m}$Tc generator system (Syncor, Fairfield, N.J.) as a solution of sodium pertechnetate in 0.9% sodium chloride. Rhenium-188 was obtained from a tungsten-188 ($^{188}$W/$^{188}$Re) generator system (Oak Ridge National Laboratory, Oak Ridge, Tenn.) as a solution in 0.9% sodium chloride. Indium-111 was purchased as $^{111}$InCl$_3$ in 0.1M HCl from NEN-DuPont (Boston, Mass.). Yttrium-88 was obtained as $^{88}$YCl$_3$ in 6M HCl from NEN-DuPont. Iodine-125 was obtained from NEN-DuPont.

Radioiodination was carried out with $^{125}$iodine using the iodogen method as previously described. See Fraker et al., Biochem. Biophys. Res. Comm. 80:849 (1978). For $^{99m}$Tc- and $^{188}$Re-labeling, the lyophilized antibody fragments prepared as described above were reconstituted with sodium pertechnetate or perrhenate in 0.9% saline. Labeling with $^{111}$indium and $^{88}$yttrium was carried out by standard methods. See, for example, "Advanced Methods for Radiolabeling Monoclonal Antibodies with Therapeutic Radionuclides" in Goldenberg, supra.

Determination of Reduction of Kidney Uptake of Radioactivity

Female BALB/c mice, 19 to 22 g of weight, 4 to 5 weeks of age (Charles River Laboratories, Boston, Mass.) were used as non-tumor-bearing animals. For a human tumor xenograft model, the human colon carcinoma cell line GW39 (Primus et al. supra) was grown subcutaneously in 5- to 6 week-old female athymic mice (Harlan, Madison, Wis.). Animals were injected intravenously into the tail vein with approximately 5–10 μg of antibody fragment protein (i.e., 25–40 μCi of $^{99m}$Tc, $^{188}$Re, and $^{111}$In, resp.; 4 μCi of $^{88}$Y, and 10 μCi of $^{125}$I, respectively).

The mice were sacrificed after 4 h and 24 h for $^{99m}$Tc-labeled antibodies, and after 4, 24, 72, 96 and 168 h for $^{125}$I, $^{111}$In, $^{88}$Y and $^{188}$Re-labeled antibodies. Mice were sacrificed by anesthesia with sodium pentobarbital and bled by cardiac puncture. After cervical dislocation, the animals were dissected. Radioactivity in the tumors and tissues (liver, spleen, kidney, lung, intestine, blood and bone) was determined by gamma scintillation counting using an injection standard to correct for physical decay.

For determination of whole-body clearance and organ uptake kinetics in humans, the ROI (region of interest) technique was applied onto whole-body scans obtained at 10 min, 1 h, and 24 h after antibody administration (Siemens BODYSCAN, Siemens Gammasonics, Erlangen, FRG). Geometric means were calculated, and after correction for radioactive decay, all values were expressed in percent of injected dose by referring to the whole-body counts at 10 min p.i. without previous voiding of the urinary bladder (by definition 100% of the injected dose).

Preparation of Amino Acid Solutions

L-lysine, D-lysine and L-arginine monohydrochloride salts (Sigma, St. Louis, Mo.) were dissolved in phosphate-buffered saline (PBS) at a concentration of 160 mg/ml. L-lysine ethyl ester dihydrochloride was dissolved in PBS to yield a concentration of 80 mg/ml. Poly-L-lysine (1–4 kDa and 15–30 kDa) were used as hydrochloride salts at concentration of 25 mg/ml and 10 mg/ml, respectively.

A commercially available amino acid solution (PERIAMIN™ X™, Pfrimmer -Kabi-Pharmacia, Erlangen, FRG, containing 8.2 g L-lysine/l and 12 g L-arginine/l.), intended for parenteral nutrition of patients was used as an amino acid source in human patients.

EXAMPLE 1

Reduction in Kidney Uptake by Lysine and/or Poly-lysine

Administration of Lysine and Poly-lysine-containing Solutions

Animals were injected with the lysine and/or poly-lysine solutions intraperitoneally in amounts and at frequencies as shown below. Human patients were infused intravenously over a three-hour period with 1.5 liters of a commercially available amino acid solution starting 15 min before the antibody injection. The data of a total of 77 patients examined with $^{99m}$Tc-labeled anti-CEA Fab' (NP-4: n=19; F023C5: n=58) were taken as controls (infused with the same volume of 0.9% saline instead of the amino acid solution).

EXAMPLE 2

Effect of L-lysine on Kidney Uptake

A. In mice

Figure 1:
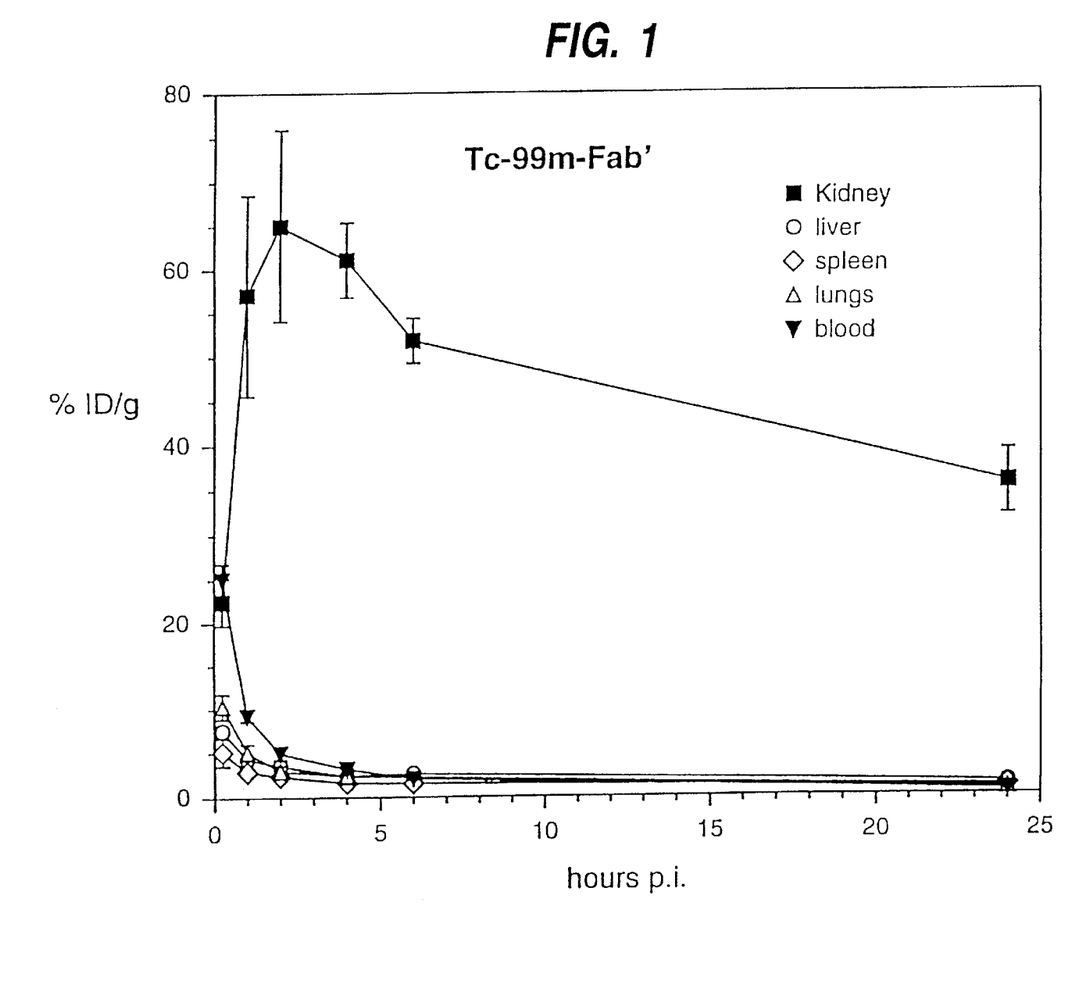
FIG. 1 shows the kidney uptake kinetics and organ distribution of $^{99m}$Tc-Fab' NP-4 in BALB/c mice.

Typical kidney uptake and organ kinetics of radiolabeled Fab' and F(ab')$_2$ fragments are shown in FIG. 1. $^{99m}$Tc-labeled Fab' fragments showed a rapid renal uptake, reaching a maximum at 2 h after intravenous antibody injection. At this time-point a plateau was reached, lasting approximately until 4–6h p.i., after which excretion of originally retained activity predominated. Peak values of kidney uptake ranged from 65.0±10.9 % ID/g to 120±15% % ID/g, accounting for an absolute uptake in both kidneys of in between 18 and 35 percent of the originally injected activity. F(ab')$_2$—kinetics With Y and In labeled F(ab)2 there is a continuous uptake up to 24 h p.i., reaching its highest value at about 55% of the injected dose /g for In, and about 43% of the injected dose /g for the Y label, with subsequent wash-out.

Figure 2A:
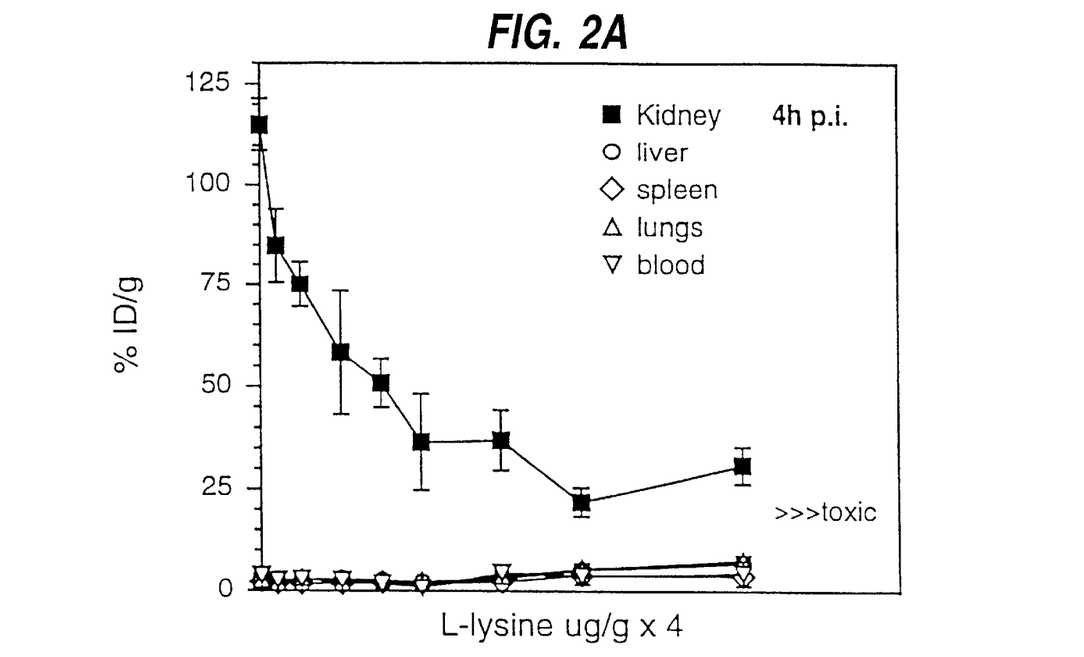
FIGS. 2A and 2B shows the dose-effect relationship between L-lysine hydrochloride, administered intraperitoneally in hourly intervals, and the kidney uptake of $^{99m}$Tc-labeled Fab' fragments of the anti-CEA MAb NP-4 in BALB/c mice, after 4h (FIG. 2A) or 24h (FIG. 2B) post-injection.
Figure 2B:
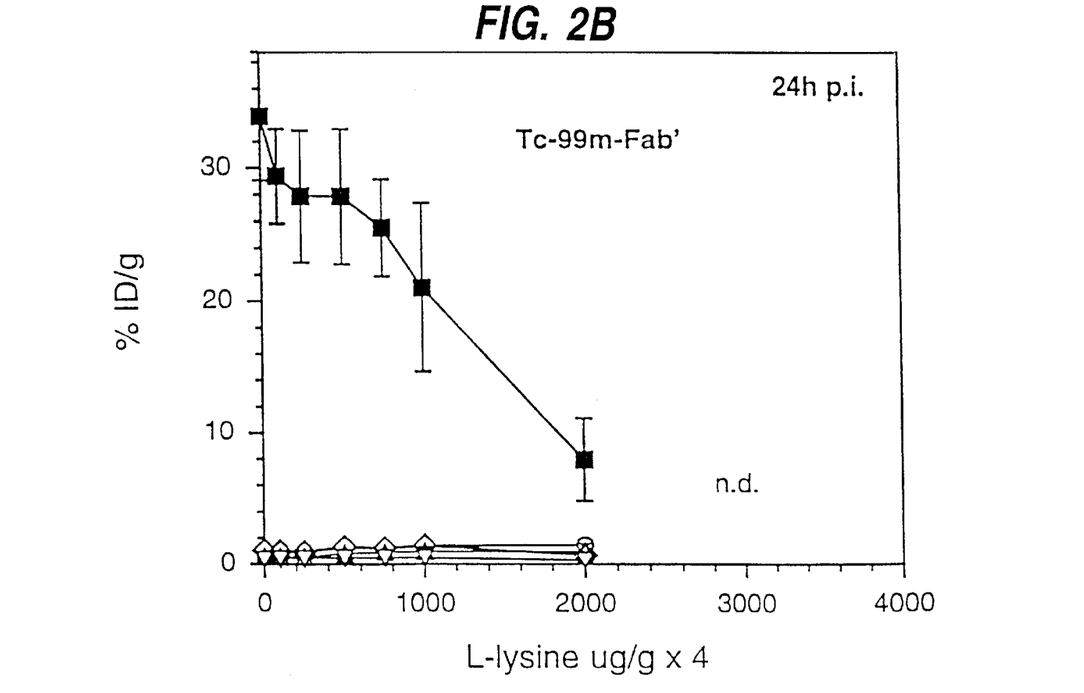

FIG. 2 shows the dose-effect relationship between L-lysine, administered i.p., and the kidney uptake of $^{99m}$Tc-labeled Fab' fragments of the monoclonal anti-CEA antibody NP-4 in BALB/c mice. L-lysine was injected i.p. in hourly intervals from 30 min before until 3 h after intravenous antibody injections (−30', 1 h, 2 h, 3 h p.i.). Doses below four times 100 µg/g body weight (given in hourly intervals), produced no significant effect could be observed. At doses above this threshold, a strong dose-effect relationship was found. At 4×2000 µg/g, kidney uptake was reduced to 19±1% of the untreated control group at 4 h p.i. The maximum tolerated dose (MTD) of L-lysine in mice was reached at 4×2500 µg/g (injected i.p. in hourly intervals). This dose was tolerated without any obvious short or long term toxicity (monitored for three months). At higher doses, the mice began to develop fluid in the body cavities (e.g. pleural effusions). No additional effect on kidney uptake was observed in lysine doses above this MTD (see FIG. 2).

The effect of uptake reduction of $^{99m}$Tc-Fab' persisted for 24 hours. This effect was obscured somewhat because in the control group 50–70% of the originally retained technetium had been excreted at this time-point, and therefore lysine-induced reduction appeared less profound than at earlier time-points.

In nude mice bearing human colonic xenografts, no significant influence on the tumor uptake or uptake in any other organ than the kidneys was seen by the lysine treatment (see Table 1).

Less frequent L-lysine administration (once 30 min before antibody administration or twice 30 min before and 1 h after antibody injection) was significantly less effective than the four injections in hourly intervals. For example, a single injection at 30 min. before antibody administration reduced kidney uptake of Tc-Fab' only to 56.4% of the control amount, and two injections (at 30 min. before and 1 h after antibody) reduced kidney uptake to 44.1% of the control amount. In comparison, four injections reduced kidney uptake to 15.5% of control. See Table 2.

Figure 3:
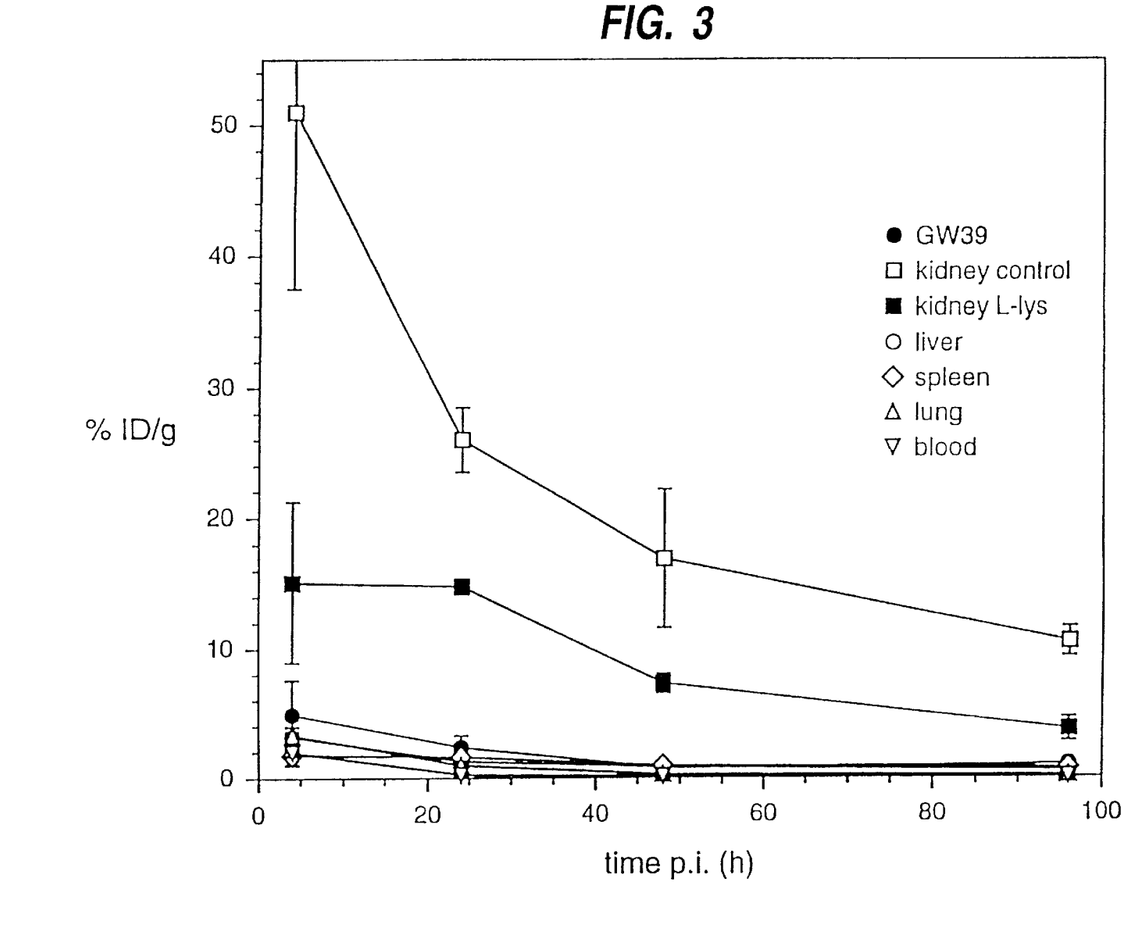
FIG. 3 shows the effect of L-lysine treatment on kidney uptake of directly $^{188}$Re-labeled anti-CSAp Mu-9 Fab' in nude mice bearing GW39 colonic cancer xenografts.

L-lysine had comparable effects on $^{188}$Re-labeled Fab' fragments of the anti-CSAp antibody Mu-9. See FIG. 3. Lysine treatment reduced kidney uptake to 29% of the untreated control after 4 h p.i. No effect on the uptake in the tumor or other organs was observed. Table 3 summarizes the dosimetry of $^{188}$Re-Mu-9 Fab' under control and lysine treatment conditions. The kidney dose under lysine-treatment is approximately 30% of the renal dose in the control group, whereas no effect on the tumor dose could be observed.

Figure 4A:
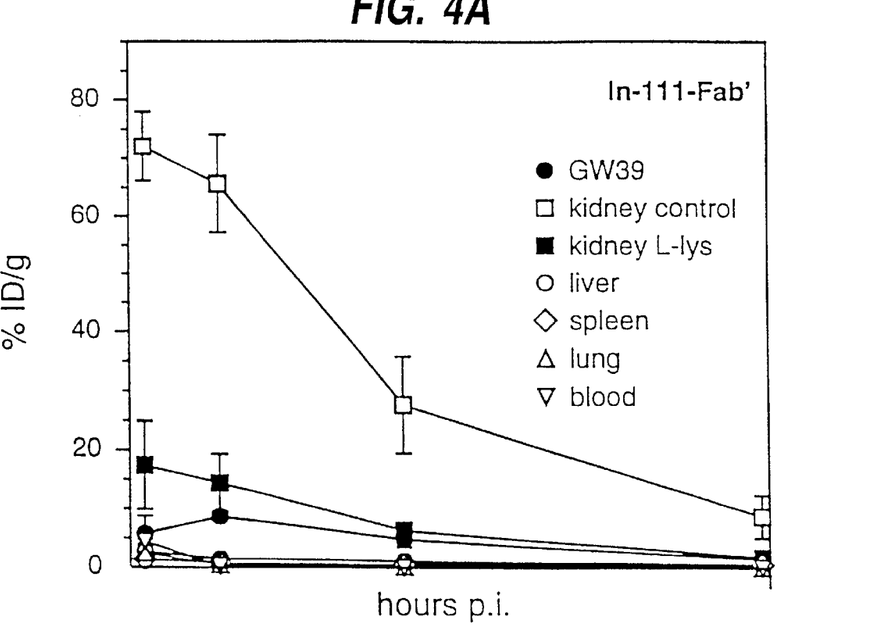
FIGS. 4A and 4B shows the effect of L-lysine treatment on kidney uptake of $^{111}$In (FIG. 4A) and $^{88}$Y-Bz-DTPA (FIG. 4B) labeled Fab' MN-14 in GW39 bearing nude mice colonic cancer xenografts.
Figure 4B:
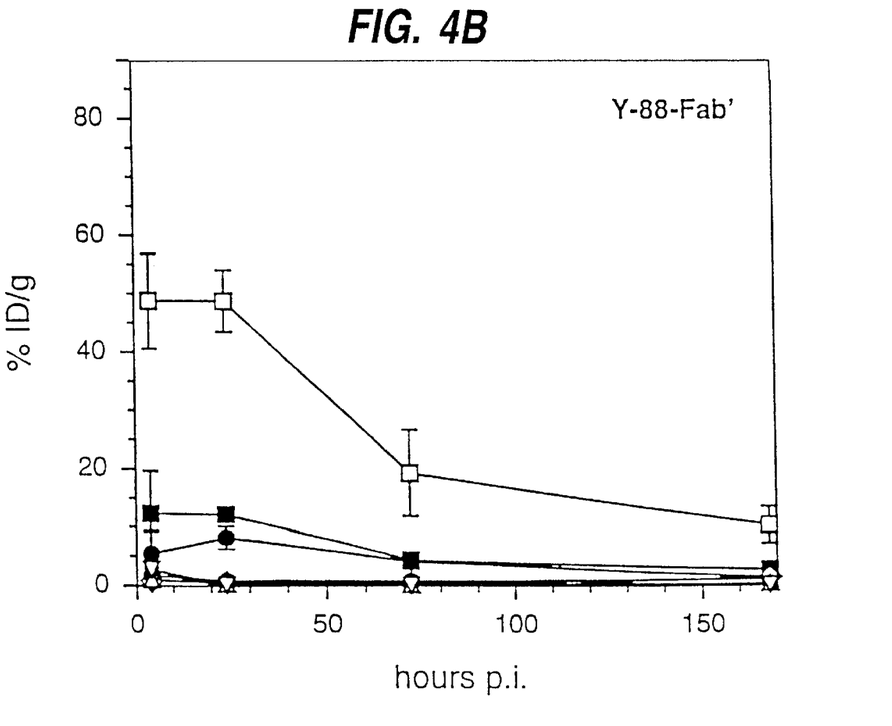

To test the effectiveness of L-lysine in reduction of kidney uptake of indium and yttrium-labeled Fab' fragments, a mixture of $^{111}$In and $^{88}$Y-labeled Fab' fragments of the anti-CEA antibody MN-14 were injected into GW39 colon carcinoma bearing nude mice (injected with four times 2000 µg/g L-lysine; the control group were untreated). FIG. 4 and Table 4 summarize the results.

Lysine also reduced the kidney uptake of Fab' fragments labeled with isotopes that are not retained significantly by cells (e.g. iodine). Table 5 summarizes the organ kinetics of an $^{125}$I-labeled Fab' fragment of NP-4. Although the kidney uptake of iodine-labeled Fab' was found much lower than with all radiometals, it was still reduced by L-lysine to 38.7% of the nontreated control at 4 h p.i., which results in a 50% reduction of the absorbed dose to the kidney, calculated for a $^{131}$I-labeled Fab' fragment.

Figure 6A:
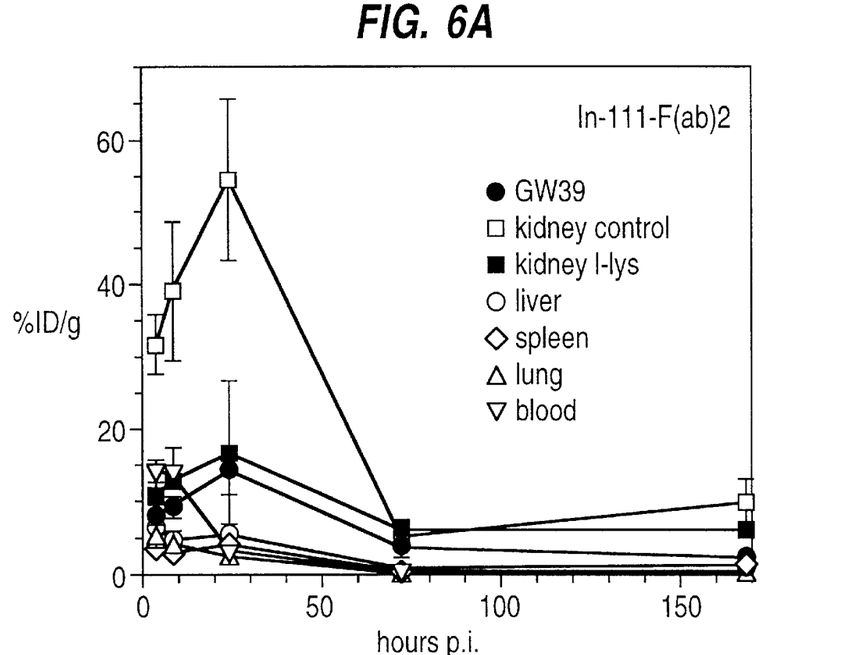
FIGS. 6A and 6B shows a time course of the effect of L-lysine on reduction of kidney uptake of $^{88}$Y FIG. 6A and $^{111}$In-labeled FIG. 6B F(ab)$_2$ fragments of the anti-CEA antibody MN-14.
Figure 6B:
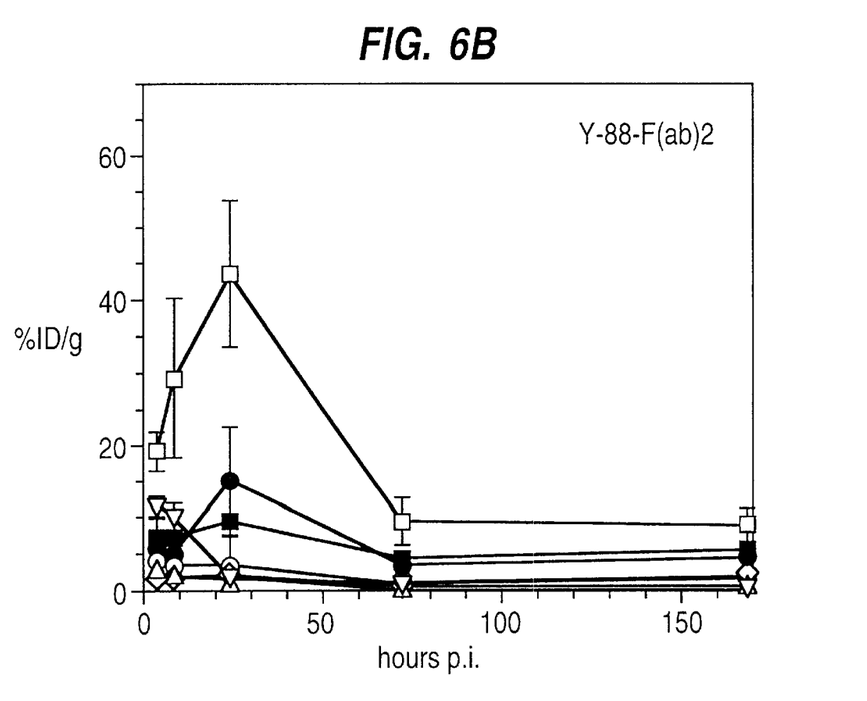

FIG. 6 and Table 6 summarize the reduction of kidney uptake observed with F(ab')$_2$ fragments. Uptake with $^{111}$In- and $^{88}$Y- F(ab')$_2$ was reduced to approximately 30% of control by lysine treatment. As was observed with Fab' fragments, reduction of uptake persisted for several days. See FIG. 6.

TABLE 1

Dose-effect relationship of treatment with L-lysine and poly-L-lysine (1–4 kD) in GW39 colonic cancer xenograft bearing nude mice with anti-CEA $^{99m}$Tc-Fab' NP-4

| | | L-lysine | | poly-L-lys |
| --- | --- | --- | --- | --- |
| | control | 0.5 mg/g lys injection i.p. at −30', 1, 2, 3 h | 2 mg/g lys injection i.p. at −30', 1, 2, 3 h | 0.15 mg/g poly i.v. at −30' |
| 4 h p.i. | | | | |
| GW39 | 3.5 ± 0.6 | 3.2 ± 0.5 | 5.0 ± 1.9 | 3.0 ± 1.0 |
| liver | 2.0 ± 0.3 | 1.6 ± 0.2 | 1.8 ± 1.1 | 1.5 ± 0.2 |
| spleen | 1.3 ± 0.1 | 1.0 ± 0.1 | 1.3 ± 0.1 | 1.0 ± 0.1 |
| kidney | 58.9 ± 9.6 | 37.1 ± 3.7 | 17.5 ± 4.3 | 30.8 ± 6.0 |
| % of contr. | 100.0 | 63.0 | 29.7 | 52.2 |
| lung | 3.1 ± 0.2 | 5.4 ± 1.3 | 4.5 ± 1.4 | 3.1 ± 1.2 |
| blood | 1.7 ± 0.3 | 1.6 ± 0.2 | 1.9 ± 0.2 | 1.7 ± 0.2 |
| 24 h p.i. | | | | |
| GW39 | 1.7 ± 0.2 | 1.9 ± 0.5 | 2.2 ± 0.6 | 2.2 ± 0.3 |
| liver | 1.0 ± 0.1 | 0.9 ± 0.2 | 1.4 ± 0.3 | 0.9 ± 0.1 |
| spleen | 0.6 ± 0.1 | 0.5 ± 0.3 | 0.7 ± 0.3 | 0.7 ± 0.1 |
| kidney | 26.7 ± 3.6 | 18.7 ± 3.9 | 8.0 ± 3.2 | 25.3 ± 5.7 |
| % of contr. | 100.0 | 70.0 | 30.0 | 94.7 |
| lung | 0.3 ± 0.1 | 0.4 ± 0.2 | 0.9 ± 0.6 | 0.8 ± 0.6 |
| blood | 0.3 ± 0.0 | 0.5 ± 0.3 | 0.3 ± 0.1 | 0.3 ± 0.0 |

TABLE 2

Effect of less frequent administration of L-lysine on the biodistribution of $^{99m}$Tc-Fab' NP-4 in BALB/c mice (uptake values in % ID/g at 4 h p.i.)

| | | L-lysine (2000 µg/g) | | |
| --- | --- | --- | --- | --- |
| organ | control | injection once at −30' | injection twice at −30' and 1 h | injection 4x at 30', 1, 2, 3 h |
| liver | 2.5 ± 0.3 | 4.9 ± 2.4 | 2.7 ± 0.5 | 2.2 ± 0.5 |
| spleen | 2.3 ± 0.2 | 3.2 ± 1.2 | 2.0 ± 0.2 | 1.4 ± 0.4 |
| kidney | 122.6 ± 20.8 | 69.1 ± 9.8 | 54.1 ± 6.0 | 19.0 ± 5.7 |
| % of contr. | 100.0 | 56.4 | 44.1 | 15.5 |
| lung | 3.4 ± 0.2 | 6.2 ± 3.8 | 4.6 ± 1.7 | 2.1 ± 0.9 |
| blood | 3.3 ± 0.4 | 4.3 ± 1.8 | 3.0 ± 0.6 | 2.4 ± 0.4 |

TABLE 3

Dosimetry of $^{188}$Re-Fab' Mu-9

| | control | | L-lysine | | |
| --- | --- | --- | --- | --- | --- |
| | cGy/mCi | T/NT | cGy/mCi | T/NT | lys/contr. |
| GW39 | 620.3 | | 763.4 | | 1.23 |
| liver | 611.3 | 1.01 | 587.6 | 1.30 | 0.96 |
| spleen | 306.0 | 2.03 | 289.0 | 2.64 | 0.94 |

TABLE 3-continued

Dosimetry of $^{188}$Re-Fab' Mu-9

| | control | | L-lysine | | |
|---|---|---|---|---|---|
| | cGy/mCi | T/NT | cGy/mCi | T/NT | lys/contr. |
| kidney | 7818.8 | 0.08 | 3085.2 | 0.25 | 0.39 |
| lung | 537.7 | 1.73 | 410.4 | 1.86 | 0.76 |
| blood | 256.4 | 2.42 | 203.1 | 3.76 | 0.79 |
| bone | 120.9 | 5.13 | 107.3 | 7.11 | 0.89 |

TABLE 4

Effect of treatment with L-lysine (four times 2000 μg/g i.p.) on the dosimetry of anti-CEA Fab' MN-14 in GW39 colonic cancer xenograft bearing nude mice. A mixture of $^{111}$In and $^{88}$Y-labeled Bz-DTPA-Fab' was injected. The $^{90}$Y-dosimetry was calculated based on the $^{88}$Y and $^{111}$In-biodistribution separately.

| | control | | | L-lysine | | |
|---|---|---|---|---|---|---|
| | cGy/mCi based on | | T/NT | cGy/mCi based on | | T/NT |
| | $^{111}$In | $^{88}$Y | yttrium | $^{111}$In | $^{88}$Y | yttrium |
| GW39 | 5668.8 | 4953.8 | | 6478.1 | 5751.1 | |
| liver | 1736.1 | 1339.9 | 3.70 | 2096.8 | 1651.9 | 3.48 |
| spleen | 607.6 | 626.9 | 7.90 | 564.5 | 499.2 | 11.52 |
| kidney | 34245.3 | 33057.2 | 0.15 | 7849.0 | 6231.0 | 0.93 |
| | 100% | 100% | | 22.9% | 18.8% | |
| lung | 501.0 | 385.6 | 12.85 | 662.8 | 431.1 | 13.3 |
| blood | 751.2 | 493.6 | 10.04 | 985.5 | 664.1 | 8.66 |
| intestine | 737.1 | 519.9 | 9.53 | 768.1 | 560.2 | 10.26 |
| bone | 391.2 | 493.2 | 10.04 | 508.7 | 588.4 | 9.77 |
| washed bone | 187.0 | 396.7 | 12.49 | 277.6 | 486.8 | 11.81 |

TABLE 5

Effect of L-lysine (4 × 2 mg/g) on the kidney uptake of $^{125}$I-labeled Fab' NP-4 and the dosimetry for a $^{131}$I-labeled Fab'

| | $^{131}$I-Fab' NP-4 | | |
|---|---|---|---|
| organ | control cGy/mCi | L-lysine cGy/mCi | lys/control |
| liver | 81.9 | 77.2 | 0.94 |
| spleen | 51.8 | 42.1 | 0.81 |
| kidney | 229.5 | 116.6 | 0.51 |
| lung | 126.4 | 120.2 | 0.95 |
| blood | 117.7 | 116.6 | 0.99 |

TABLE 6

Effectiveness of L-lysine on the kidney uptake and the dosimetry of yttrium-labeled F(ab')$_2$ fragments of the anti-CD22 antibody LL2

| | % ID/g 4 h p.i. | | % ID/g 48 h p.i. | | dose (cGy/mCi) | |
|---|---|---|---|---|---|---|
| organ | contr. | lys | contr. | lys | contr. | lys |
| liver | 5.9 ± 0.5 | 8.8 ± 1.6 | 4.0 ± 0.2 | 4.5 ± 0.5 | 4509.8 | 5375.0 |
| spleen | 3.1 ± 0.3 | 3.5 ± 0.7 | 3.9 ± 0.5 | 3.8 ± 0.6 | 2989.2 | 3031.9 |
| kidney | 22.9 ± 2.8 | 13.4 ± 0.8 | 26.2 ± 4.3 | 13.0 ± 1.6 | 21230.7 | 10813.9 |
| % control | 100.0 | 58.5 | 100.0 | 49.6 | 100.0 | 50.9 |
| lungs | 5.2 ± 0.9 | 6.9 ± 2.4 | 1.9 ± 0.3 | 1.9 ± 0.2 | 1777.8 | 2192.1 |
| blood | 13.4 ± 2.4 | 12.8 ± 4.7 | 1.5 ± 0.2 | 1.4 ± 0.2 | 4146.4 | 3651.3 |

B. In Humans

Figure 7A:
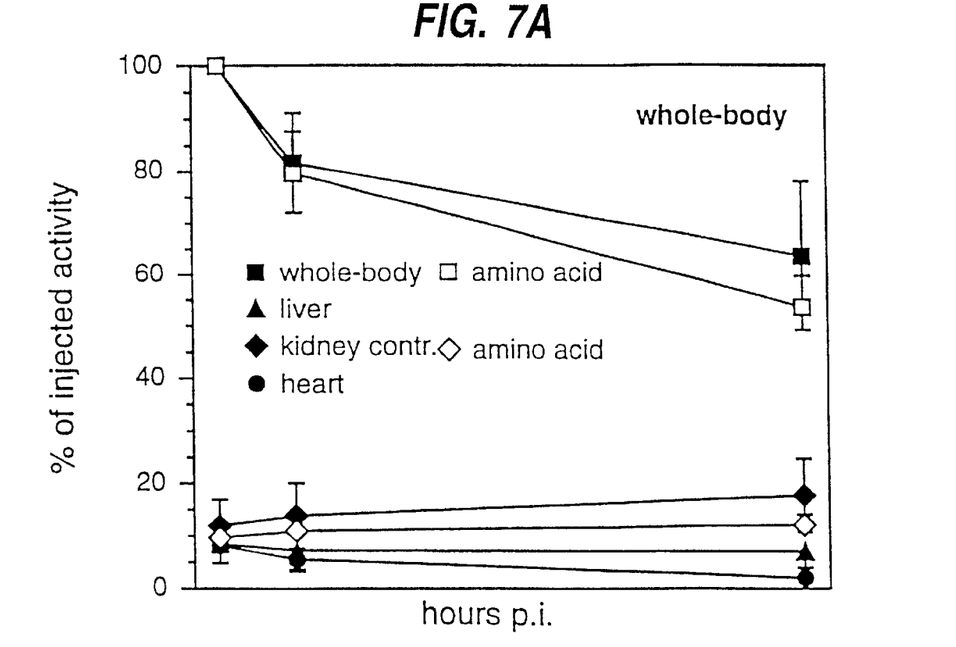
FIGS. 7A and 7B shows the effects of a commercially available amino acid solution (containing 1.75 g of L-lysine) on kidney uptake in five patients undergoing RAID studies with $^{99m}$Tc-Fab' fragments of the anti-CEA MAbs F023C5 and NP-4. Control patients were given an equal volume of saline.
Figure 7B:
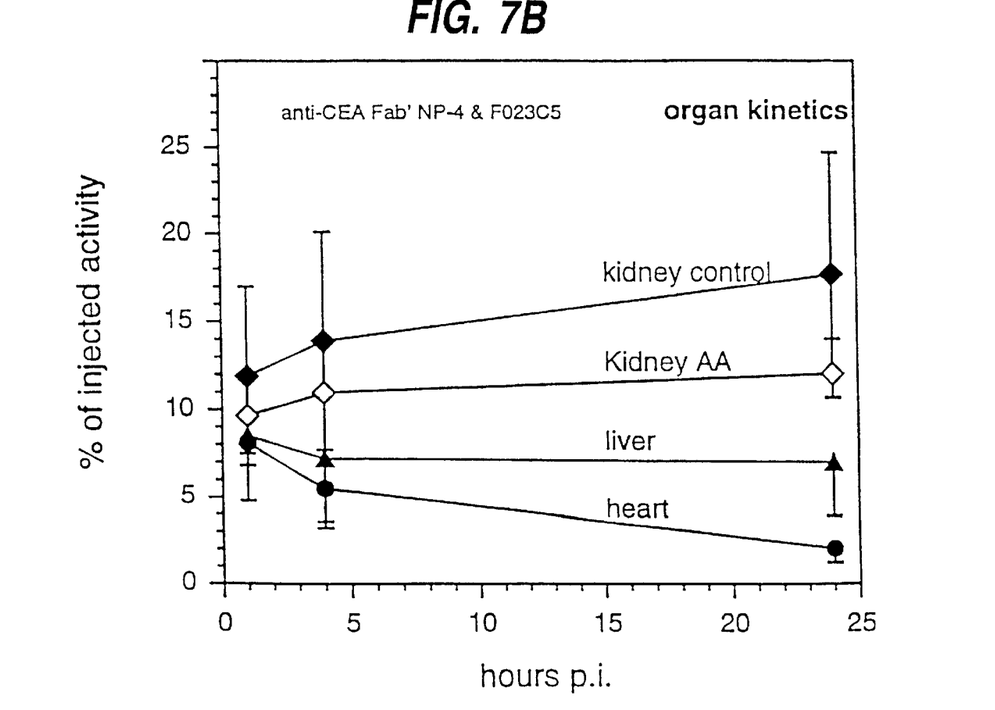

Five patients undergoing radioimmunodetection studies with $^{99m}$Tc-labeled Fab' fragments of two anti-CEA antibodies were infused over a three-hour period with a commercially available amino acid solution, containing a total of 1.75 g of L-lysine and 3.75 g of L-arginine as basic amino acids. Quantification of organ uptake kinetics showed a decrease of kidney uptake. See FIG. 7. This effect was more pronounced at 24 than at 4 h p.i. Whole-body retention showed slightly lower values in the treated patients.

EXAMPLE 3

Effect of D-lysine on Kidney Uptake

D-lysine was tested under the same conditions as L-lysine (four hourly injections i.p.). D-lysine was found to be equally as effective as the L-isomer in lowering kidney uptake.

EXAMPLE 4

Effect of polymeric Lysine Compounds

To attempt to reduce the necessity of frequent injections of the kidney uptake reducing agent, polymeric substances of higher molecular weight were investigated. The results obtained are summarized in Table 7. Poly-L-lysine with a molecular weight range of 1–4 kDa reduced kidney uptake with a single i.p. injection at significantly lower doses than the monomer. However, the MTD was reached at 300 μg/g, so that the possible maximal absolute uptake reduction was less than with the monomer. The potency of poly-L-lysine increased with increasing molecular weight. L-lysine of molecular weight 15–30 kDa showed 50% uptake reduction at 1×20 μg/g (MTD 20 μg/g).

TABLE 7

Effect of poly-L-lysine of different molecular weight on the biodistribution of $^{99m}$Tc-Fab' NP-4 at 4 h p.i.

| organ | control | 1–4 kD | | | 15–30 kD | |
|---|---|---|---|---|---|---|
| | | 100 μg/g | 200 μg/g | 300 μg/g | 10 μg/g | 20 μg/g |
| | | poly-L-lysine administered once 30' before antibody | | | | |
| liver | 3.4 ± 0.4 | 3.0 ± 0.2 | 3.0 ± 0.4 | 3.5 ± 0.8 | 7.3 ± 3.7 | 4.6 ± 0.7 |
| spleen | 2.1 ± 1.1 | 3.0 ± 0.4 | 2.7 ± 0.4 | 3.5 ± 0.4 | 3.7 ± 0.4 | 3.8 ± 0.3 |
| kidney | 127.7 ± 15.7 | 95.5 ± 4.3 | 80.5 ± 6.9 | 67.9 ± 7.5 | 73.9 ± 7.2 | 55.7 ± 6.5 |
| % control | 100.0 | 74.8 | 63.0 | 53.2 | 57.8 | 43.6 |
| lungs | 7.7 ± 1.3 | 5.9 ± 3.1 | 3.9 ± 2.6 | 5.6 ± 1.0 | 6.8 ± 4.3 | 7.9 ± 3.2 |
| blood | 5.1 ± 0.4 | 3.8 ± 0.1 | 4.4 ± 0.5 | 5.3 ± 1.4 | 4.7 ± 0.3 | 4.7 ± 0.2 |
| | | poly-L-lysine administered twice (30' before and 1 h after antibody) | | | | |
| kidney | 73.0 ± 6.0 | | | 43.7 ± 10.0 | | 41.6 ± 8.8 |
| % control | 100.0 | | | 59.9 | | 56.9 |

EXAMPLE 5

Effect of Mixtures of Monomeric and Polymeric Lysine Compounds

Figure 5:
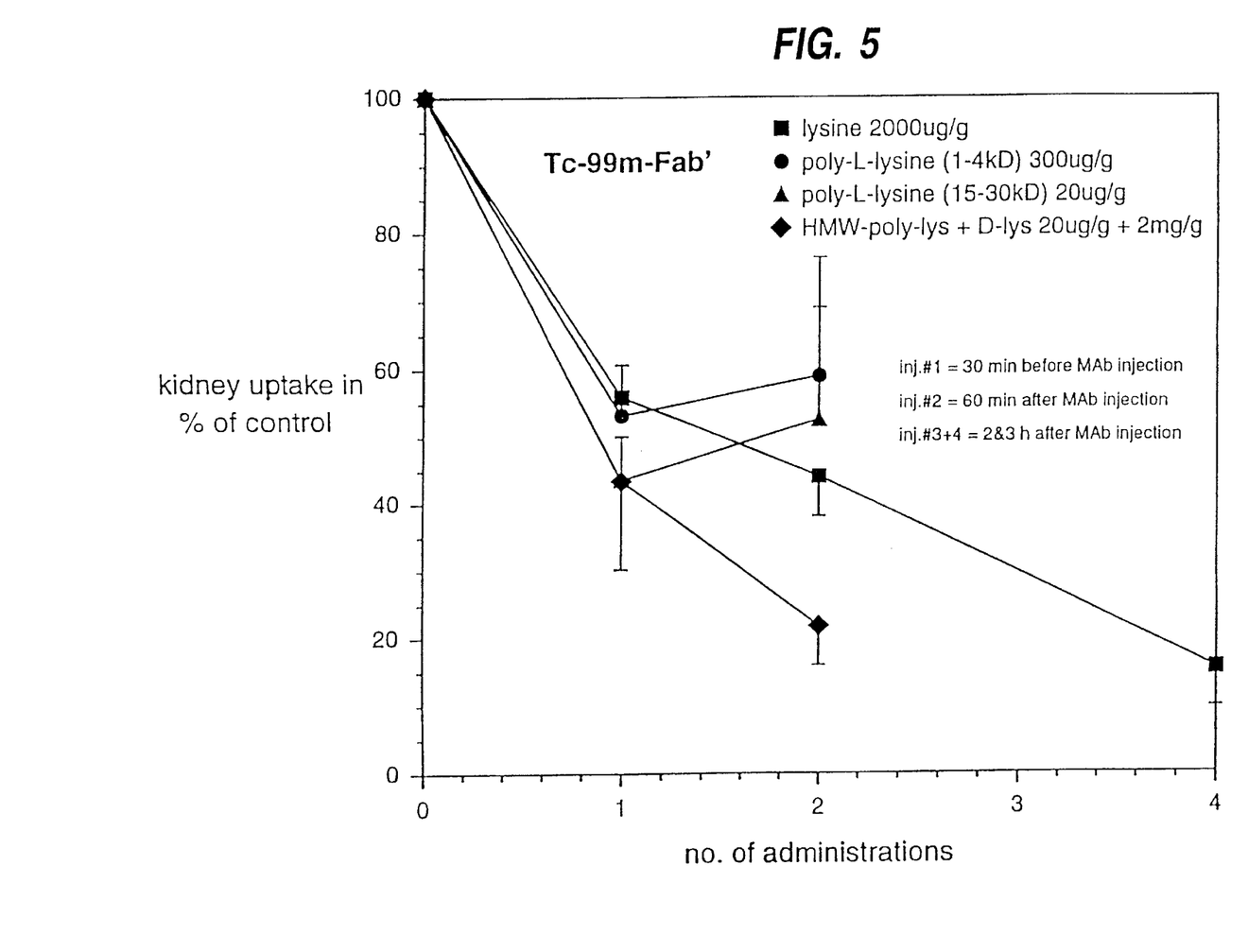
FIG. 5 shows the effect of the frequency of the intraperitoneal administration of lysine, poly-L-lysine and mixtures thereof on the kidney uptake of 99mTc-Fab' NP-4.

To reach maximal effectiveness with as few injections as possible, combinations of lysine and poly-lysine were tested. The results obtained are summarized in FIG. 5. Optimal results were found with two injections of a mixture of 2 mg/g lysine and 20 μg/g poly-lysine (15–30 kDa) at 30 min. before and 1 h after antibody administration. Despite the fact that both compounds were given close to their individual maximum tolerated dose, no acute or long-term toxicities could be noticed during monitoring for three months after treatment.

EXAMPLE 6

Diagnostic Imaging of Lymphoma

A posterior abdomen scan of a patient with a gastric carcinoma in the antral region and liver metastasis in the left hepatic lobe who underwent RAID with $^{99m}$Tc Fab' fragment of FO23C5 (Sorin Biomedical, Saluggia, Italy) and was infused with PERIAMIN™ (see above). The kidney image obtained at 4h and 24h p.i. was much less intense than usually observed with fragments and therefore the primary tumor, which was adjacent to the left kidney, was readily visualized.

The invention has been disclosed broadly and illustrated in reference to representative embodiments described above. Those skilled in the art will recognize that various modifications can be made to the present invention without departing from the spirit and scope thereof.

What is claimed is:

1. A method of reducing kidney retention of antigen binding antibody fragment conjugates in a patient during radioimmunodiagnosis or immunotherapy, comprising administering to said patient an effective amount of one or more compounds selected from the group consisting of D-lysine molecule, poly-lysine molecule and pharmaceutically acceptable salts thereof, wherein the poly-lysine molecule and the pharmaceutically acceptable salts thereof comprise poly-D-lysine or poly-L-lysine and have a molecular weight in the range of 1–60 kDa, whereby said compound or compounds reduce kidney retention of said antibody fragment conjugates.

2. The method according to claim 1, wherein D-lysine is administered to said patient.

3. The method according to claim 1, wherein poly-D-lysine is administered to said patient.

4. The method according to claim 1, wherein poly-L-lysine is administered to said patient.

5. The method according to claim 1, wherein a mixture of at least two of said compounds is administered to said patient.

6. The method according to claim 1, wherein said poly-lysine molecule has a molecular weight in the range of 15–30 kDa.

7. The method according to claim 1, wherein said compound is parenterally administered to said patient in a physiologically acceptable aqueous solution.

8. The method according to claim 7, wherein said compound in a physiologically acceptable aqueous solution is administered to said patient by continuous infusion.

9. The method according to claim 7, wherein said compound in a physiologically acceptable aqueous solution is administered to said patient by means of at least one injection of a bolus of said solution.

10. The method according to claim 1, wherein said antibody fragment confugates comprise a radiolabel.

11. The method according to claim 10, wherein the radiolabel is an imaging isotope, and wherein said patient is undergoing radioimmunodiagnosis.

12. The method according to claim 10, wherein the conjugates comprise a cytotoxic agent and wherein said patient is undergoing immunotherapy.

* * * * *